United States Patent [19]

Carvalho da Silva

[11] Patent Number: 5,560,371

[45] Date of Patent: Oct. 1, 1996

[54] INSTRUMENT FOR MEASURING THE PEAK FLOW DURING AN EXHALATION

[75] Inventor: Jose Carvalho da Silva, Schönau, Germany

[73] Assignee: Jedermann & Pohl GmbH, Germany

[21] Appl. No.: 288,696

[22] Filed: Aug. 15, 1994

[30] Foreign Application Priority Data

Aug. 14, 1993 [DE] Germany .......................... 43 27 446.3

[51] Int. Cl.$^6$ .................................................. A61B 5/087
[52] U.S. Cl. .............................. 128/725; 128/727; 482/13
[58] Field of Search ..................... 128/725, 727; 482/13

[56] References Cited

U.S. PATENT DOCUMENTS

| 4,041,935 | 8/1977 | Garbe ........................................ 482/13 |
| 5,224,487 | 7/1993 | Bellofetto et al. .................... 128/725 |

FOREIGN PATENT DOCUMENTS

| 2625093 | 6/1989 | France .................................. 128/725 |
| 9221163 | 11/1992 | WIPO . |
| 9306778 | 4/1993 | WIPO . |

*Primary Examiner*—Lee S. Cohen

*Attorney, Agent, or Firm*—Michael D. Bednarek; Kilpatrick & Cody

[57] ABSTRACT

An instrument for measuring the peak flow during an exhalation, which can be quickly and simply assembled and disassembled manually, so that a simple and cost effective production is possible, on the one hand, and a complete cleaning of the instrument is possible on the other hand, so that a hygienic use is guaranteed. The case of the instrument consists of two halves (12 and 22). The first half (12) of the case is equipped with a projection (18), which locks into a recess (24) in the second half (22) of the case when the case is assembled. The two halves of the case (12 and 22) are furthermore both equipped with an extension piece (22 or 26, respectively), with the two extension pieces resting on each other when the case is assembled. For the assembly, the projection (18) installed on the second half (22) of the case is rotated into the recess (24) in the second half of the case, so that the two halves (12 and 22) of the case are joined and the two extension pieces (20 and 26) rest on each other. A holding element is then slipped onto the two extension pieces (20 and 26) and detachably locked with a securing element. For the disassembly, the securing element is removed from the holding element, the holding element from the two superposed extension pieces (20 and 26) and the two halves of the case (12 and 22) then rotated apart, so that the projection (18) slides out of the recess (24).

21 Claims, 4 Drawing Sheets

INSTRUMENT FOR MEASURING THE PEAK FLOW DURING AN EXHALATION

FIELD OF THE INVENTION

The invention is based on an instrument for measuring the peak flow during an exhalation.

BACKGROUND OF THE INVENTION

Instruments, which are called "peak-flow-meters", are known in general and are used by a treating physician in the therapeutic monitoring of the lung function where the expiratory peak exhalation speed plays a significant role. An instrument of the above described type is known, for instance, from DE 24 33 994 A1 in which a rod installed in the case is permanently fastened in a case wall with one end, and in which the receptacle for a mouth piece, which is plugged onto the air inlet opening, is screwed onto the other end of the rod. An instrument of the above mentioned type is known from U.S. Pat. No. 4,944,306, in which the two halves of the case and the receptacle for a mouth piece are firmly welded to each other and the rod is permanently installed inside the case. Instruments of the above mentioned type are further known, in which the halves of the case are screwed onto each other, for example, and the receptacle for the mouth piece is fastened on the inlet opening with fixing devices which cannot be detached manually.

Assembly of all of these known instruments is difficult and cumbersome because of their design, and in some instances only possible with tools. Furthermore, also due to their design, all of these known instruments can only be cleaned with difficulty or not at all, since they can either not be disassembled at all or only very awkwardly with tools. A complete disassembly of the instruments, however, is absolutely necessary for the thorough and complete cleaning of the same, since the warm and humid exhalation air blown into the instrument creates extremely favorable conditions for the growth of bacteria and fungi inside the instruments, which can only be removed by a thorough cleaning of the individual parts.

SUMMARY OF THE INVENTION

The task of the present invention therefore is the further development of a peak-flow meter instrument so that it can easily and cost-effectively be manually assembled and disassembled without tools and thus offers the preconditions for a complete cleaning and hygienical use.

This task is solved with a peak-flow meter in which a first half of its case is equipped with at least one projector which locks into a recess of a second half. In accordance with the invention, the first and second halves of the case are respectively equipped with at least one extension piece which rest on each other when the case is assembled. The extension pieces are held together detachably through a holding element slipped over the same when the case is assembled.

Easy assembly and disassembly of the instrument is achieved through the fact that one half of the case has at least one projection which engages into a cut-out in the other half of the case when the case is put together, that the first and second half of the case each have at least one extension piece which rest against each other when the case is assembled, and that the two extension pieces are held together with a securing element which is slid over the two extension pieces when the case is put together.

This design of the case allows for a simple and quick assembly of the instrument without tools, so that a significant cost advantage is achieved in the production of the instrument. After the instrument has been used, it can easily be disassembled manually with little physical effort and be assembled again without difficulty after cleaning due to this design of the case, so that this can also be done by elderly or ill persons and children and the pre-conditions are given for a hygienical use of the instrument.

The extension pieces installed at the respective halves of the case are preferably designed such as to enclose the air inlet opening when the case is assembled.

In a preferred design, the receptacle for the mouth piece is designed as a holding element which holds the two extension pieces together and is slipped onto the extension pieces which enclose the air inlet opening. Through this design the receptacle fulfills two tasks, so that an additional component is eliminated, assembly and disassembly become even easier due to the reduced number of components, and a further cost advantage is achieved in the manufacture of the instrument. The receptacle for the mouth piece consists of a hollow body according to a preferred design, which has an opening on both of the front sides facing each other. The mouth piece is inserted into the first opening and is held in the receptacle through known, self-locking insert slopes, for instance, permitting a simple and problem-free exchange of the mouth piece. Into the second opening the superposed extension pieces of the two case halves are inserted. Through this special design of the mouth piece receptacle, the superposed extension pieces are completely enclosed and thus held together firmly and securely when the instrument is in use.

The receptacle for the mouth piece is advantageously detachably secured to the two extension pieces with a securing element in order to prevent an accidental removal of the mouth piece receptacle designed as a holding element, and thus prevent an accidental opening of the case. In a special design, this securing element is designed in the shape of a bracket and is provided with protruding ribs on both sides that project on the inside and protrude beyond the ends of the sides with noses. Furthermore, these ribs projecting to the inside are equipped with at least one projection protruding further to the inside. The mouth piece receptacle consisting of a hollow body preferably has two openings opposite each other in the surface area, which are installed in indentations, whereby the sides of the bracket-shaped securing element are inserted into the indentations. The ribs of the securing element are thus inserted through the openings in the indentations of the surface area into recesses advantageously installed on the extension pieces of the two case halves. In order to secure the bracket-shaped securing element, it is inserted into the indentations on the surface area of the holding element until the noses at the ends of the ribs lock behind the surface area of the holding element from the inside and the projections installed at the ribs lock into place in the cut-outs advantageously provided in the recesses of the extension pieces. In this manner a detachable form closure is achieved which can be manually unlocked and put back together with little physical effort. This results—through the eliminated tools for the assembly and disassembly—in a cost advantage in the production, as already mentioned above, on the one hand, and in the fact that cleaning, also mentioned above, becomes possible to guarantee a hygienical use, on the other hand.

The projection installed on the one half of the case, which locks into a cut-out in the second half of the case when the case is put together, is preferably designed as a projecting locking nose and locks into a cut-out provided as air outlet opening in the second half of the case.

Through this special design of the locking nose in connection with the extension pieces held together through a holding element which is detachably locked onto the two extension pieces through a securing element, the case can be simply and easily assembled and disassembled. In order to assemble the case, the locking nose installed on a first half of the case is rotated into the interlocking opening on the second half of the case, so that the two halves of the case are placed together and the two extension pieces rest on each other. The holding element is then slipped onto the two extension pieces and locked detachably with the securing element. For the disassembly, the securing element is removed from the holding element, the holding element is removed from the two superposed extension pieces and the two halves of the case are then moved apart, so that the locking nose slips out of the interlocking opening.

In order to guarantee the simple and easy assembly and disassembly of the rod and the baffle plate installed in the case and the spring element installed between the case and the baffle plate, which is necessary for a complete cleaning of all components of the instrument, the spring element preferably consists of a coil spring, which is installed around the rod installed in the case. In a particularly advantageous design, this coil spring is equipped with a hook which projects into the interior of the coil spring and intersects the center axis of the coil spring and which is wedged with one end of the rod between the rod and a diffuser installed in the air inlet opening.

In a particularly preferred design, the other end of the coil spring is screwed onto the baffle plate. For this purpose, the baffle plate advantageously is equipped with a bored-through collar installed vertically to the surface, through which the rod is inserted and onto which the end of the coil spring is slipped. Furthermore, a boring is installed next to the collar in an advantageous design, leading vertically through the baffle plate, at which a threaded portion starts which is installed on the baffle plate surface and leads around the collar once, with an ascending gradient corresponding to the ascending gradient of the coil spring. In order to mount the coil spring on the baffle plate, one end of the coil spring is slipped onto the bored-through collar which is preferably designed with a conical exterior shape, until the end of the coil spring rests on the threaded portion formed on the baffle plate surface. The coil spring is then turned so that the end of the wire forming the coil spring slides along the threaded portion until it reaches the boring which is installed in the threaded portion and leads through the baffle plate surface, and then turned further through the boring until it reaches the back of the threaded portion. Through further turning of the coil spring, any desired amount of winds of the wire forming the coil spring can now be moved to the back of the baffle plate, so that the length of the part of the coil spring installed between baffle plate and diffuser can be exactly adjusted.

In this way a simple and quick assembly and disassembly of coil spring, baffle plate and rod are possible on the one hand, and coil springs of different lengths, caused by manufacturing variations, for instance, can be adjusted to a determined length, on the other hand. It is also possible to use coil springs with different spring characteristics which can be adjusted to the required spring resistance due to the spring being screwed onto the baffle plate, as in the described design.

BRIEF DESCRIPTION OF THE DRAWINGS

A preferred design of the invention is described in more detail in connection with the drawings in which.

DETAILED DESCRIPTION

The parts described in the following have been assigned the same reference numbers in all drawing figures in which they are shown.

Figure 1:
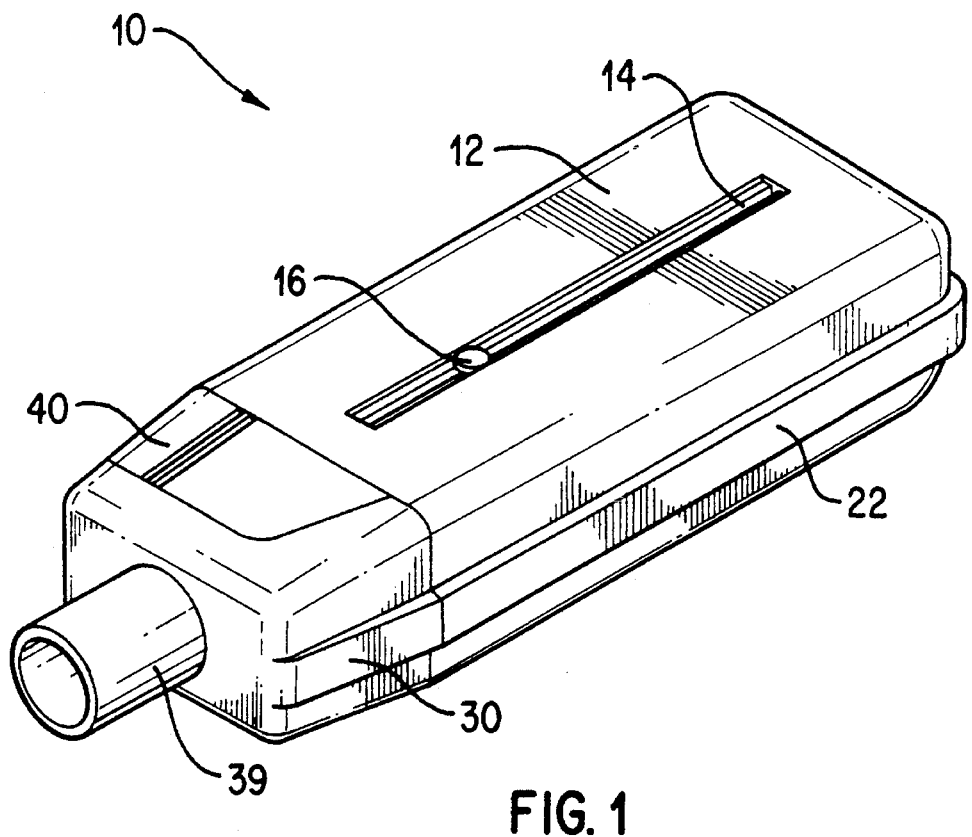
FIG. 1 is a perspective view of the instrument for measuring the peak flow during an exhalation.

FIG. 1 shows a perspective view of an assembled instrument 10. The case of instrument 10 consists of two case halves, a top half 12 and a bottom half 22. The top half of the case 12 has a slot 14 extending along part of the length of the case in which a reading element 16 is installed, which is movable along the slot. Depending on the volume of the air flow during exhalation, the reading element 16 will take a certain position in slot 14. One or two scales (not shown) installed beside the slot then allow for the measured value to be read in units, such as, e.g. 1/min or 1/sec. At its front end, instrument 10 is equipped with a receptacle 30 for a mouth piece 39 which is fastened to the case with a securing element 40.

Figure 1A:
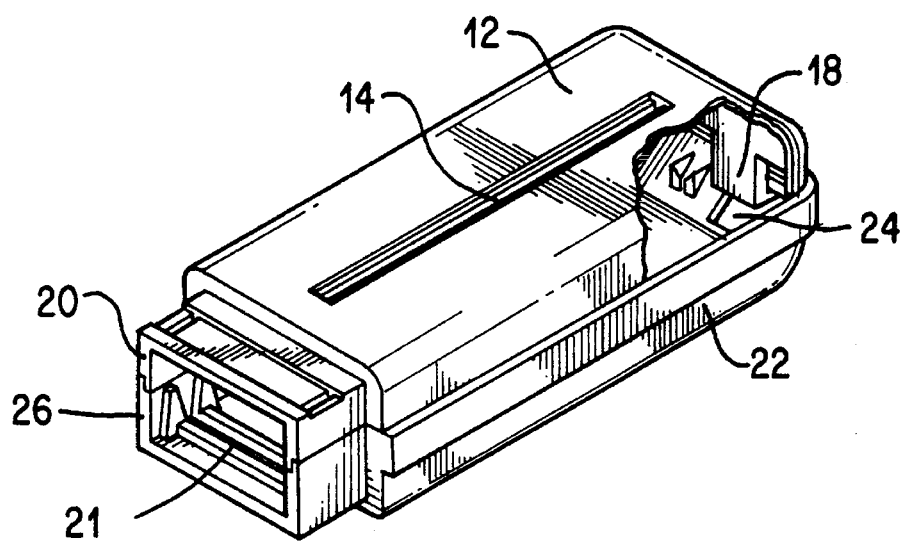
FIG. 1A is a perspective view of the two assembled halves of the instrument case with partial cut-away.

FIG. 1A shows a perspective view of the two assembled halves of the case of instrument 10. The top half 12 of the case is shown here as a partial cut-away, in order to be able to clearly depict the projection 18. The top half 12 of the case has the slot 14 extending alongside the case, as well as two projections 18, which are formed as protruding noses, one of which is visible through the cut-away. At its front end, the top half 12 of the case is equipped with an extension piece 20. The bottom half 22 of the case is also equipped with an extension piece 26 at its front end. When the case is assembled, the two extension pieces 20 and 26 rest on each other, as shown, so that they enclose the air inlet opening 21. At its back end, the bottom half 22 of the case is equipped with two air outlet openings 24, into which the protruding noses 18 of the top half 12 of the case lock when the halves of the case are put together.

Figure 2:
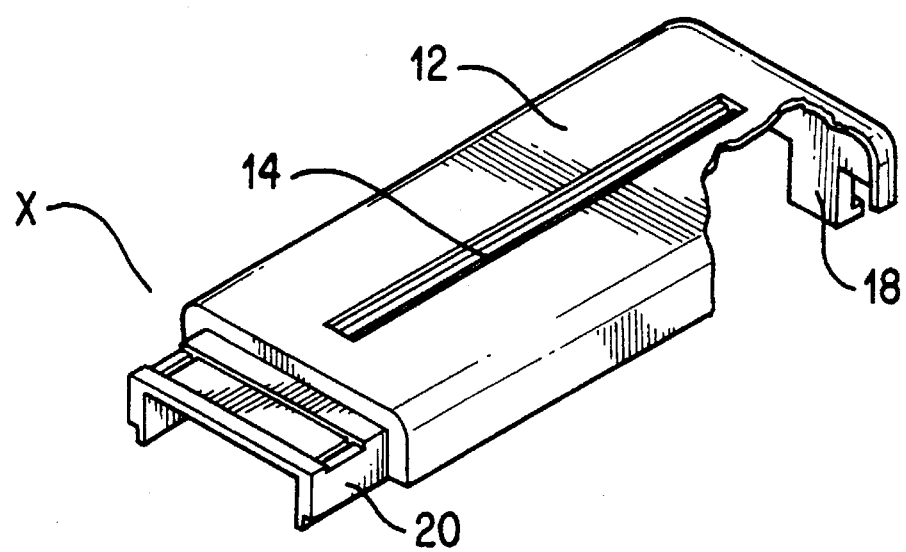
FIG. 2 is a perspective view of the top half of the instrument case.

FIG. 2 shows a perspective view of the top half 12 of the case with a cut-away, in order to be able to depict one of the two protruding noses 18 installed at its back end.

Figure 3:
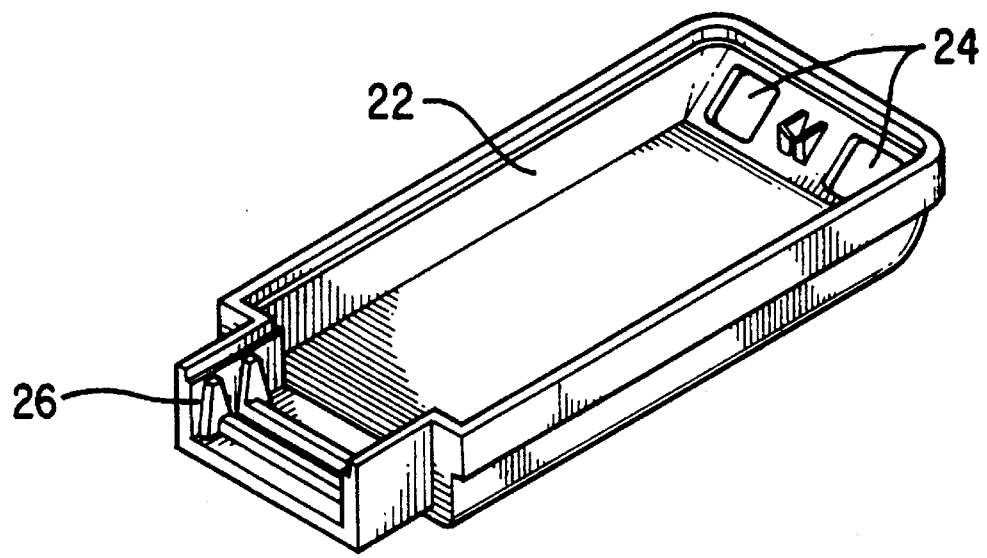
FIG. 3 is a perspective view of the bottom half of the instrument case.

FIG. 3 shows a bottom half 22 of a case in the perspective. At the back end of the half 22 of the case, the two air outlet openings 24 are installed, into which the protruding noses 18 of the top half 12 of the case lock when the two halves of the case are joined together.

Figure 4:
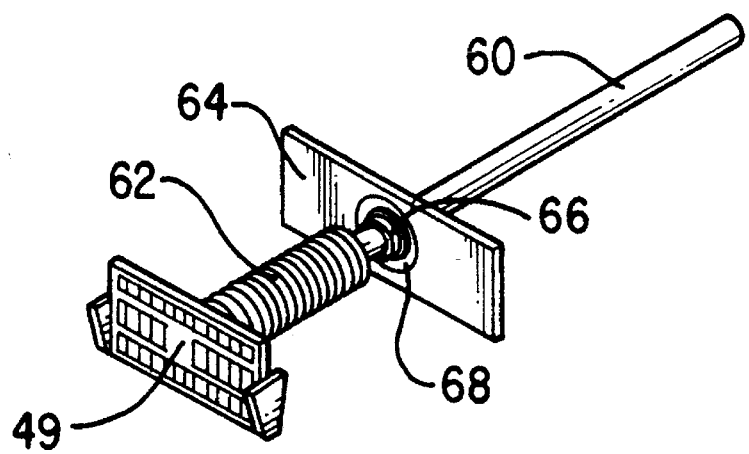
FIG. 4 is a perspective view of the rod with baffle plate, coil spring and diffuser in the assembled state.

FIG. 4 shows the rod 60 with the baffle plate 64, coil spring 62 and diffuser 19 in the perspective in their functional positions. The baffle plate 64 has a bored-through collar 66, installed vertically to the surface, with which the baffle plate 64 is mounted on rod 60 in a fashion so that it can slide. One end of the rod 60 is mounted in the diffuser 19. Between diffuser 19 and baffle plate 64, a coil spring 22 is installed around the rod 60. One end of the coil spring 62 is equipped with a hook which projects into the inside of the coil spring and intersects with the center axis of the coil spring and which is wedged between the coil spring and the diffuser 19 with one end of the rod 60. The other end of the coil spring 62 is screwed onto the baffle plate 64. For this purpose, the collar 66 on the baffle plate 64 projects from the surface in direction of the diffuser and has a conic shape. Around this collar a threaded portion 68 is designed on the baffle plate surface, which leads around the collar once and has an ascending gradient corresponding to the ascending gradient of the coil spring 62. The end of the coil spring 62 to be fastened to the baffle plate 64 is slipped onto the collar 66, until it rests against the threaded portion 68. The wire forming the end of the coil spring is then led through a boring installed in the threaded portion 68 through turning of the coil spring 62, so that through further turning, the coil spring 62 is screwed into the threaded portion 68 and thus into the baffle plate 64.

Figure 5:
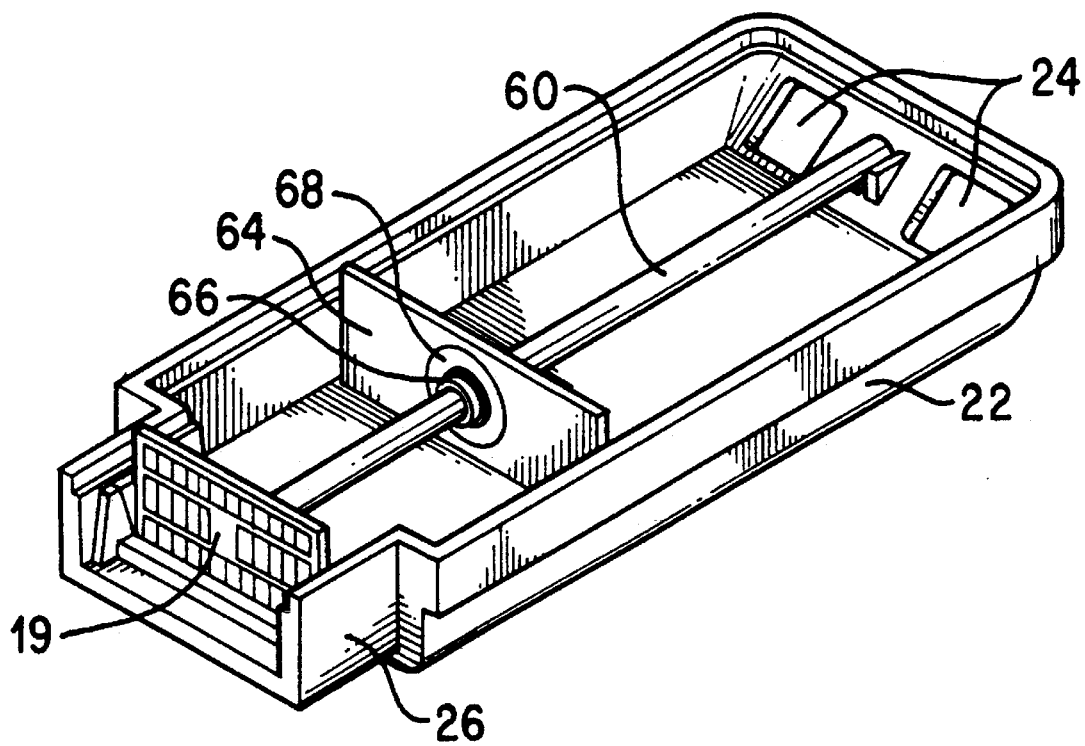
FIG. 5 is a perspective view of the bottom half of the case with rod, baffle plate and diffuser according to FIG. 4 in assembled condition.

FIG. 5 shows the bottom half 22 of the case with rod 60, baffle plate 64 and diffuser 19 in their installed positions. The diffuser 19, which connects one end of the rod 60, is inserted into the extension piece 26. The second end of the rod 60 is mounted at the back end of the half 22 of the case.

Figure 6:
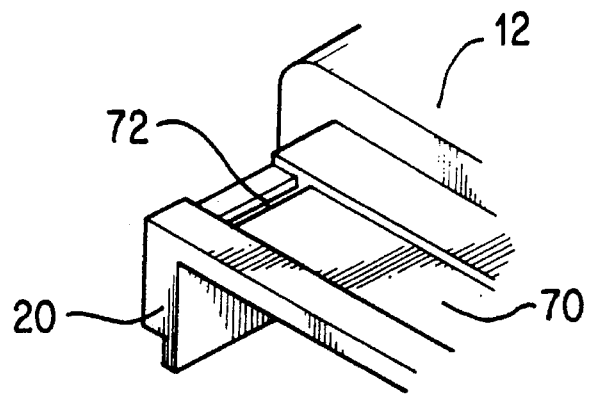
FIG. 6 is an enlarged perspective drawing of detail X of FIG. 2.

FIG. 6 is an enlarged perspective view of detail X of FIG. 2. This view shows the recess 70 installed in the extension piece 20 of the top half 12 of the case. This recess 70, which is equipped with a cut-out 72 at each end, is also installed at the extension piece 26 of the bottom half 22 of the case in the surface pointing to the outside when the case is assembled.

Figure 7:
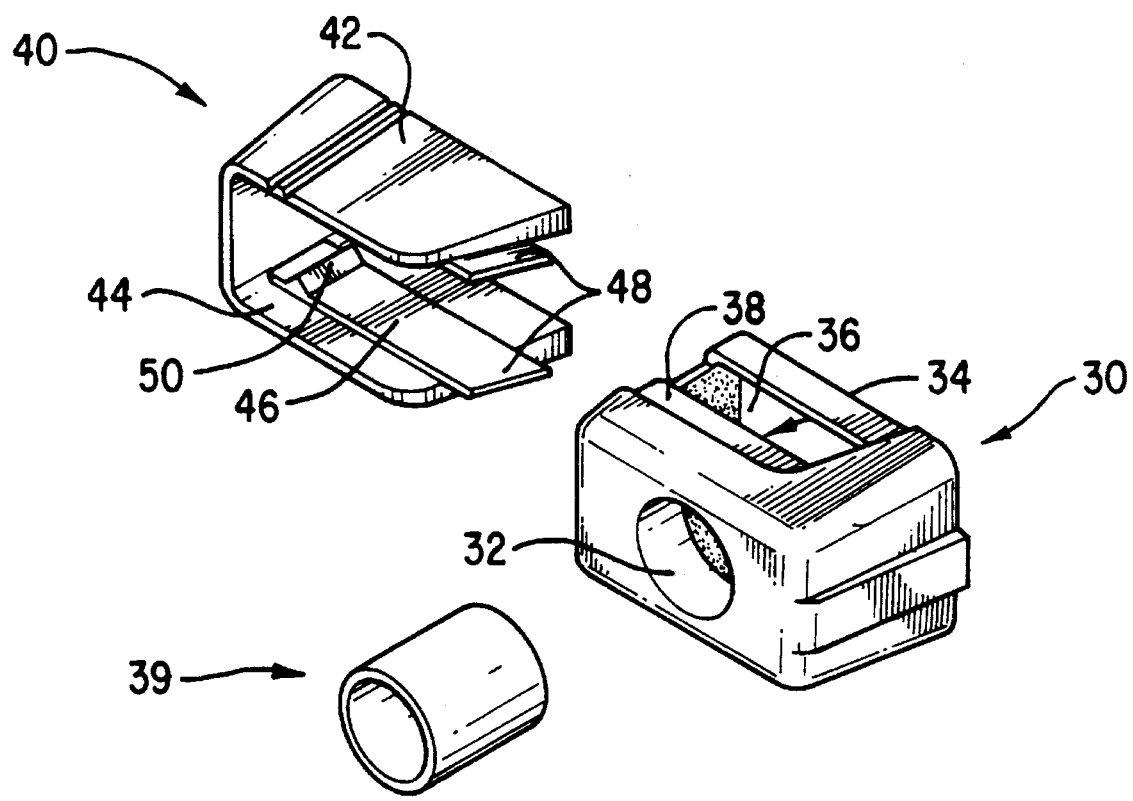
FIG. 7 is a perspective view of the holding element, the securing element and the mouth piece.

FIG. 7 shows the receptacle 30 for a mouth piece 39, which is designed as a holding element, together with the securing element 40 and the mouth piece 39 in the perspective. The receptacle 30 consists of a hollow body which is equipped with an opening 32, 34, respectively, at the two opposite front sides. Into the first opening 32, the mouth piece 39 is inserted, with the second opening 34 the receptacle 30 is slipped onto the two superposed extension pieces 20 and 26 of the two case halves 12 and 22. At its surface area, the receptacle 30 is equipped with two openings 36 across from each other, which are installed in indentations 38. Into these indentations 38, the bracket-shaped securing element 40 is inserted. The bracket-shaped securing element 40 is equipped with a rib 46 on the two sides 42 and 44, respectively, which projects to the inside and protrudes with a nose 48 beyond the ends of the sides 42 and 44. In the area of the end of the rib 46 directed towards the inside, the rib is equipped with a projection 50 protruding further to the inside. When the bracket-shaped securing element 40 is inserted into the indentations 38 of the receptacle 30, the ribs 46 are pushed through the openings 36 into the recesses 70 on the extension pieces 20 and 26 of the two halves of the case 12, 22. During this process, the noses 48 of the ribs 46 lock behind the surface area of the receptacle 30 from the inside and the projections 50 on the ribs 46 lock into the cut-outs 72 in the recesses 70 which are installed on the extension pieces 20 and 26.

In this manner, an interlocking connection is formed between the securing element 40, holding element 30 and the halves of the case 12, 22 resting on each other, which can be unlocked manually with little physical effort, so that the instrument 10 can, for instance, also be easily disassembled and re-assembled for cleaning purposes by children and ill or elderly persons. During the production, too, the instrument can be easily, quickly and thus cost effectively assembled in the above described manner.

What is claimed is:

1. Instrument for measuring the peak flow during an exhalation, consisting of:
    a case comprised of two case halves, an air inlet opening and at least one air outlet opening, as well as a slot extending alongside a portion of the case with a moveable reading element installed along the slot,
    a rod installed inside the case, which extends from the inlet opening into the case in a direction parallel to the slot and which has a baffle plate glide-mounted thereon, the movable reading element being movable by the baffle plate along the slot;
    a spring element which is installed between the case and the baffle plate and which creates an increasing spring resistance to the movement of the baffle plate away from the inlet opening; and
    a mouth piece which is installed on the case in the area of the air inlet opening, said mouth piece being in communication with the air inlet opening;
    wherein the first half of the case is equipped with at least one projection and the second half of the case is equipped with a recess, and wherein said at least one projection locks into said recess,
    the first half and the second half of the case are equipped with at least one extension piece, respectively, which rest on each other, and
    a holding element slipped over the two extension pieces, said holding element detachably holding the two extension pieces together.

2. Instrument according to claim 1, wherein the two extension pieces are equipped with at least one recess, respectively, at a surface of said two extension pieces pointing to the outside, and the recesses are equipped with at least one cut-out.

3. Instrument according to claim 1, wherein the two extension pieces enclose the air inlet opening.

4. Instrument according to claim 3, wherein the holding element comprises a receptacle for the mouth piece which holds the two extension pieces together.

5. Instrument according to claim 4, wherein the receptacle for the mouth piece consists of a hollow body having a first opening and a second opening at opposing sides whereby the mouth piece is inserted into the first opening and the extension pieces of the two halves of the case are inserted into the second opening, the hollow body further being equipped with indentations in a surface area of the hollow body between the first and second openings of the hollow body, and two additional openings in said surface area of the hollow body, the two additional openings being located across from each other and being installed in said indentations.

6. Instrument according to claim 4, further comprising a securing element, wherein the receptacle for the mouth piece is locked detachably on the two extension pieces with said securing element.

7. Instrument according to claim 6, wherein the securing element is shaped as a bracket and has two inner sides equipped with protruding ribs, said ribs having noses which extend, respectively, beyond said inner sides of said bracket shaped securing element, and said ribs having at least one projection extending perpendicularly from a surface portion thereof.

8. Instrument according to claim 7,
    wherein the two extension pieces are equipped with at least one recess, respectively, at a surface of said extension pieces pointing to the outside, and the recesses are equipped with at least one cut-out;

wherein the receptacle for the mouth piece consists of a hollow body having a first opening and a second opening at opposing sides whereby the mouth piece is inserted into the first opening and the extension pieces of the two halves of the case are inserted into the second opening, the hollow body further being equipped with indentations in a surface area of the hollow body between the first and second openings of the hollow body, and two additional openings in said surface area of the hollow body, the two additional openings being located across from each other and being installed in said indentations; and wherein the bracket-shaped securing element is inserted into the indentations on the surface area of the holding element, whereby the ribs of the securing element are inserted through the two additional openings into the recesses on the extension pieces of the two halves of the case, the noses at the ends of the ribs lock around the surface area of the holding element from the inside, and the projection of each of the ribs locks into the respective cut-out of each recess so that a manually detachable form closure is achieved between the securing element, the holding element and the extension pieces.

9. Instrument according to claim 1, wherein said at least one air outlet opening is formed in the second half of the case, and the at least one projection on the first half of the case is designed as a projecting nose, said projecting nose locking into said air outlet opening of the second half of the case.

10. Instrument according to claim 1, wherein the spring element consists of a coil spring, which is installed around the rod installed inside the case, said spring element being equipped with a hook projecting into the inside of the coil spring and intersecting with a center axis of the coil spring;

wherein said instrument further includes a diffuser disposed in the air inlet opening at one end of the rod, the coil spring abutting said diffuser at one end and being screwed onto said baffle plate.

11. Instrument according to claim 10, wherein the baffle plate is equipped with a bored-through collar installed vertically to a surface through which the rod is inserted and onto which one end of the coil spring is slipped, as well as a boring provided next to the collar which extends vertically through the baffle plate and at which a threaded portion starts which is installed on a surface of the baffle plate and leads around the collar once, said coil spring has an ascending gradient, and said threaded portion has an ascending gradient that corresponds to the ascending gradient of the coil spring.

12. A peak-flow meter comprising:

a case formed of a first half and a second half, said case including an air inlet opening and an air outlet opening;

a slot formed in said case;

a rod disposed within said case and extending parallel to said slot from said air inlet opening;

a baffle plate provided on said rod so as to move therealong;

a reading element provided on said baffle plate which is viewable through said slot;

a spring element disposed within said case which provides an increasing resistance against movement of said baffle plate away from said air inlet opening;

a mouth piece provided on said case over said air inlet opening, said mouth piece being in communication with said air inlet opening;

a projection formed in the first half of the case and a recess formed in the second half of the case, said projection locking into said recess;

a first extension piece formed with said first half of the case and a second extension piece formed with said second half of the case, the first extension piece and the second extension piece resting on each other; and a holding element slipped over said first extension piece and said second extension piece, whereby said case is detachably held together.

13. A peak-flow meter as set forth in claim 12, wherein each of said first extension piece and said second extension piece includes a cut-out portion formed on an outer surface thereof.

14. A peak-flow meter as set forth in claim 12, wherein said first extension piece and said second extension piece enclose said air inlet opening.

15. A peak-flow meter as set forth in claim 14, wherein said holding element comprises a receptacle for said mouth piece which holds said first extension piece and said second extension piece together.

16. A peak-flow meter as set forth in claim 15 wherein said receptacle comprises a hollow body having a first opening and a second opening, said mouth piece being inserted into said first opening; and wherein said first half and said second half of the case include respective superposed extension pieces which are inserted into said second opening of the receptacle.

17. A peak-flow meter as set forth in claim 15 further comprising a securing element for detachably locking said first extension piece and said second extension piece.

18. A peak-flow meter as set forth in claim 17, wherein said securing element is bracket-shaped and has two sides upon which respective protruding ribs are formed so as to matingly insert into respective indentations formed on said first extension piece and said second extension piece.

19. A peak-flow meter as set forth in claim 12 wherein said projection formed in said first half of the case locks into said air outlet opening.

20. A peak-flow meter as set forth in claim 12, further comprising a diffuser which is located at an end portion of said rod, said diffuser being disposed within said air inlet opening, wherein said spring element comprises a coil spring provided around said rod, said coil spring being attached at one end to said baffle plate and at another end to said diffuser.

21. A peak-flow meter as set forth in claim 20 wherein said baffle plate includes: a collar disposed perpendicularly with respect to a surface of said baffle plate through which said rod is inserted; a boring disposed next to said collar; and a threaded portion leading once around the collar and having an ascending gradient corresponding to an ascending gradient of said coil spring.

* * * * *